(12) United States Patent
Shodo

(10) Patent No.: US 8,880,179 B2
(45) Date of Patent: Nov. 4, 2014

(54) VISION REGENERATION ASSIST APPARATUS AND IMPLANTABLE APPARATUS

(75) Inventor: Kenzo Shodo, Kyoto (JP)

(73) Assignee: Nidek Co., Ltd., Aichi (JP)

( * ) Notice: Subject to any disclaimer, the term of this patent is extended or adjusted under 35 U.S.C. 154(b) by 99 days.

(21) Appl. No.: 12/955,971

(22) Filed: Nov. 30, 2010

(65) Prior Publication Data

US 2011/0130807 A1   Jun. 2, 2011

(30) Foreign Application Priority Data

Dec. 1, 2009  (JP) ................. 2009-273850

(51) Int. Cl.
| | |
|---|---|
| A61N 1/375 | (2006.01) |
| H05K 1/00 | (2006.01) |
| H05K 1/02 | (2006.01) |
| A61F 9/08 | (2006.01) |
| A61N 1/36 | (2006.01) |
| A61N 1/05 | (2006.01) |

(52) U.S. Cl.
CPC .............. *A61F 9/08* (2013.01); *A61N 1/36046* (2013.01); *A61N 1/0543* (2013.01)
USPC ............... 607/54; 607/53; 174/257; 174/262; 174/264

(58) Field of Classification Search
CPC ................................................. H01L 23/49827
USPC ........... 607/53, 54; 174/262–266; 439/45, 54, 439/82
See application file for complete search history.

(56) References Cited

U.S. PATENT DOCUMENTS

| | | | | |
|---|---|---|---|---|
| 5,029,242 A | * | 7/1991 | Sammet ........................ | 174/257 |
| 5,260,519 A | * | 11/1993 | Knickerbocker et al. ..... | 174/262 |
| 2005/0017347 A1 | * | 1/2005 | Morimoto et al. ............ | 257/703 |
| 2008/0058896 A1 | | 3/2008 | Terasawa et al. | |

FOREIGN PATENT DOCUMENTS

| | | |
|---|---|---|
| JP | 06-196864 | 7/1994 |
| JP | 2001-15869 A | 1/2001 |
| JP | 2008-55000 A | 3/2008 |

OTHER PUBLICATIONS

Office Action dated Sep. 25, 2013, issued by the Japanese Patent Office in corresponding Application No. 2009-273850.

* cited by examiner

*Primary Examiner* — Allen Porter, Jr.
(74) *Attorney, Agent, or Firm* — Sughrue Mion, PLLC

(57) ABSTRACT

A vision regeneration assist apparatus includes: a substrate including electrodes; a control unit; a mount that is formed from a sintered element made of an insulating material, the mount including through holes; an internal conductor that is to be filled into the through holes of the mount to electrically connect the control unit with wires extending from the electrodes. The internal conductor includes: a first conductive material which is to be filled to a predetermined depth from an opening of the through holes at the upper surface of the mount, the first conductive material which takes at least one type of conductive material, which is not fused at a sintering temperature of the mount; and a second conductive material which is formed from a conductive material that is to be filled into a remaining of the through holes, which faces the substrate, the second conductive material exhibiting biocompatibility.

10 Claims, 6 Drawing Sheets

PRIOR ART

PRIOR ART

VISION REGENERATION ASSIST APPARATUS AND IMPLANTABLE APPARATUS

BACKGROUND OF THE INVENTION

The present invention relates to an implantable apparatus for giving electrical stimulation to a body tissue, and especially relates to a vision regeneration assist apparatus for regenerating patient' vision.

A vision regeneration assist apparatus has recently been proposed as one of approaches toward treating blindness. Specifically, a device having a plurality of electrodes is implanted in an eyeball, etc. Electrical stimulation is applied to cells forming a retina, thereby regenerating patient's vision. Such a vision regeneration assist apparatus includes an internal body device that is equipped with an electrode for applying electrical stimulation to the cells forming the retina and a control unit (an integrated circuit) having a multiplexer function for controlling the electrode.

As an implantable apparatus for giving an electrical stimulation to a body tissue, an artificial middle ear for transmitting a sound wave to an auditory ossicle of a patient, a cardiac pacemaker implemented in a chest region of a patient for giving an electrical stipulation to a heart to suppress an occurrence of arrhythmic heartbeat, etc. are known.

If a body fluid invades an electronic circuit, such as an integrated circuit, provided in the internal body device, detrimental effects will be inflicted on circuit function. For this reason, device is made to protect the electronic circuit. For instance, the electronic circuit is placed on a mount made of an insulating material, such as ceramics, that exhibits superior biocompatibility; and is sealed with a metal case formed from a biocompatible, hermetic material [US 2008058896 A1 (JP-A-2008-55000)].

The electrodes provided on a substrate and the electronic circuit are electrically interconnected by wires formed from a conductive material filled in through holes of the mount. After having been filled into the through holes of the mount without clearance, such a conductive material is sintered. However, if a difference exists between the mount and the conductive material in terms of a coefficient of thermal expansion during sintering operation, distortion or cracks will become likely to arise in a surface of the mount, which will in turn affect placement of the electronic circuit. Accordingly, a material, such as silver, tungsten, or molybdenum, mixed with a predetermined additive in order to provide consistency between the mount and the conductive material in terms of a coefficient of thermal expansion has generally been used as a conductive material (see JP-A-2001-15869).

However, biocompatibility of tungsten or molybdenum (and an additive) has not been verified; therefore, it is difficult to adopt tungsten or molybdenum in consideration of a case where a body fluid invades a boundary (a clearance) between the substrate and the mount. Further, a conceivable approach is to use a material exhibiting superior biocompatibility, such as gold and platinum, for the conductive material. However, a great difference exists between the mount and the material in terms of a coefficient of thermal expansion, and a problem of cracking, distortion, etc., becomes likely to occur in the mount during sintering operation.

SUMMARY OF THE INVENTION

A technical object of one aspect of the present invention is to provide a vision regeneration assist apparatus and a implantable apparatus that maintain a superior state of electrical connection between an electronic circuit and a substrate by way of a mount and that can be implanted with high reliability for a long period of time while preventing occurrence of invasion of a body fluid into the electronic circuit.

In order to solve the problem, one aspect of the present invention has a configuration, such as that provided below.

(1) A vision regeneration assist apparatus for regenerating patient's vision by giving an electrical stimulation to cells forming a retina, the apparatus comprising:
  a substrate including a plurality of electrodes;
  a control unit that controls an electrical stimulation pulse to be transmitted to the electrodes;
  a mount that is formed from a sintered element made of an insulating material and that acts as a hermetic bottom for isolating and sealing the control unit from outside, the mount including:
    a plurality of through holes formed through the mount in a thickness direction,
    an upper surface on which the control unit is to be placed; and
    a lower surface on which the substrate is to be placed;
  an internal conductor that is to be filled into the through holes of the mount to electrically connect the control unit with wires extending from the electrodes and that includes:
    a first conductive material which is to be filled to a predetermined depth from openings of the through holes at the upper surface of the mount, the first conductive material including a primary member which takes at least one type of conductive material, which is not fused at a sintering temperature of the mount; and
    a second conductive material which is formed from a conductive material that is to be filled into a remaining of the through holes, which faces the substrate and which is not filled with the first conductive material, the second conductive material exhibiting biocompatibility.

(2) The apparatus according to (1), wherein
  the first conductive material includes a secondary member for performing adjustment in such a way that a coefficient of thermal expansion of the first conductive material approximately becomes equal to a coefficient of thermal expansion of a material forming the mount, and
  the second conductive material does not include the secondary member.

(3) The apparatus according to (2), wherein the mount is a ceramic sintered element.

(4) The apparatus according to (3), wherein the first conductive material includes at least one type of molybdenum, tungsten, and silver.

(5) The apparatus according to (4), wherein the second conductive material is platinum or gold.

(6) The apparatus according to (5), wherein a depth to which the second conductive material is filled into the substrate is determined in such a way that a body fluid invaded a boundary between the substrate and the mount does not contact the first conductive material.

(7) The apparatus according to (6), wherein the internal conductor includes a conductive connection block that is surrounded by the first and second conductive material while extending over the first conductive material and the second conductive material to connect the first conductive material to the second conductive material.

(8) An implantable apparatus for giving an electrical stimulation to a body tissue, comprising:
  a substrate including a plurality of electrodes;

a control unit that controls an electrical stimulation pulse to be transmitted to the electrodes;

a mount that is formed from a sintered element made of an insulating material and that acts as a hermetic bottom for isolating and sealing the control unit from outside, the mount including:
a plurality of through holes formed through the mount in a thickness direction,
an upper surface on which the control unit is to be placed; and
a lower surface on which the substrate is to be placed;

an internal conductor that is to be filled into the through holes of the mount to electrically connect the control unit with wires extending from the electrodes and that includes:
a first conductive material which is to be filled to a predetermined depth from openings of the through holes at the upper surface of the mount, the first conductive material including a primary member which takes at least one type of conductive material, which is not fused at a sintering temperature of the mount; and
a second conductive material which is formed from a conductive material that is to be filled into a remaining of the through holes, which faces the substrate and which is not filled with the first conductive material, the second conductive material exhibiting biocompatibility.

(9) The apparatus according to (8), wherein
the first conductive material includes a secondary member for performing adjustment in such a way that a coefficient of thermal expansion of the first conductive material approximately becomes equal to a coefficient of thermal expansion of a material forming the mount, and the second conductive material does not include the secondary member.

(10) The apparatus according to (9), wherein a depth to which the second conductive material is filled into the substrate is determined in such a way that a body fluid invaded a boundary between the substrate and the mount does not contact the first conductive material.

DETAILED DESCRIPTION OF EXEMPLARY EMBODIMENTS

Figure 1:
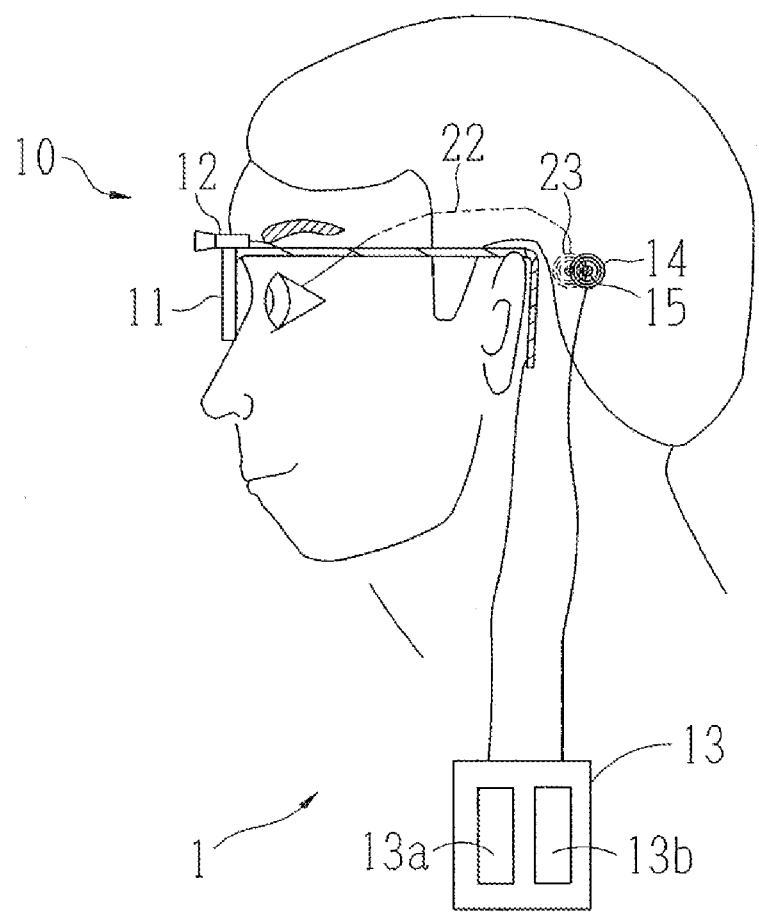
FIG. 1 is a general configuration diagram of an appearance of a vision regeneration assist apparatus.
Figure 2A:
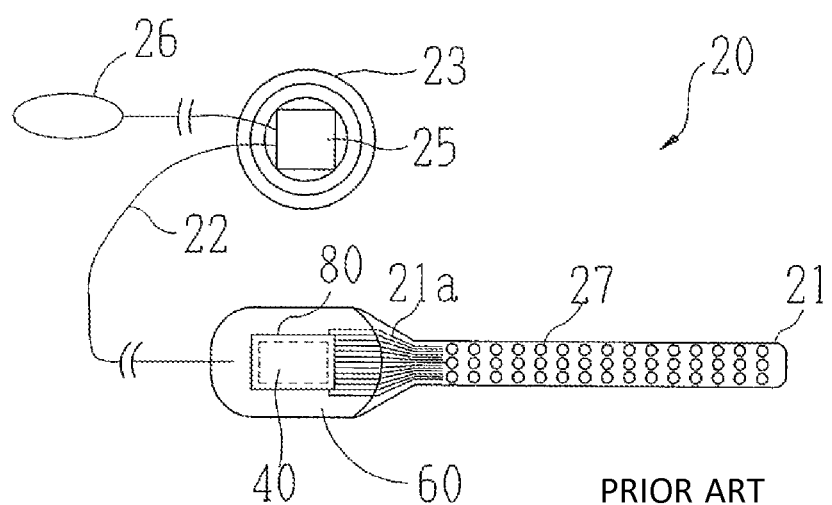
FIGS. 2A and 2B are general configuration diagrams of an internal body device of the vision regeneration assist apparatus.
Figure 2B:
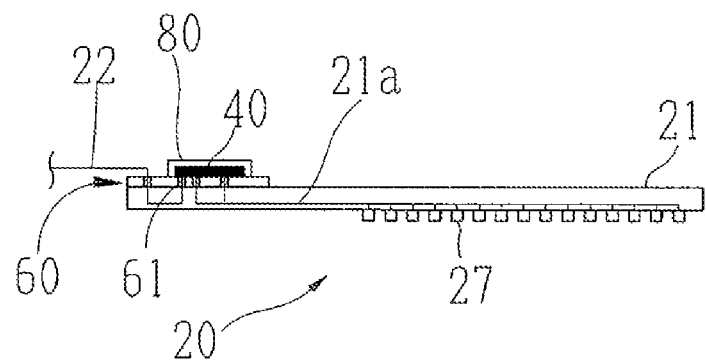

Exemplary embodiments of the present invention will be described with reference to the drawings. FIG. 1 is a general configuration diagram of an appearance of a vision regeneration assist apparatus, and FIGS. 2A and 2B are general configuration diagrams of an internal body device of the vision regeneration assist apparatus. A vision regeneration assist apparatus 1 includes an external body device 10 for taking an image of an external world and an internal body device 20 that gives an electrical stimulation to cells forming a retina, thereby promoting regeneration of vision. The external body device 10 includes a visor 11 to be worn on a patient, an image-taking device 12 made up of a CCD camera, etc., attached to the visor 11, an external device 13, a transmitter 14 made up of a primary coil, and others.

The external device 13 is provided with a pulse signal conversion unit 13a having an arithmetic processing circuit, such as a CPU, and a battery 13b for supplying electric power to the vision regeneration assist apparatus 1 (the external body device 10 and the internal body device 20). The pulse signal conversion unit 13a subjects an image of a subject captured by the image-taking device 12 to image processing and further performs processing for converting image-processed data into electrical stimulation data for regenerating vision. The transmitter 14 transmits (by wireless transmission) to the internal body device 20, in the form of an electromagnetic wave, the electrical stimulation pulse data converted by the pulse signal conversion means 13a and the electric power for activating the internal body device 20. A magnet 15 is attached to the center of the transmitter 14. The magnet 15 enhances data transmission efficiency of the transmitter 14 and is also used for securing a position with respect to a receiver 23.

As shown in FIG. 1, the visor 11 assumes a shape of eyeglasses and is used while carried on a position in front of eyes of the patient. The image-taking device 12 is attached to a front side of the visor 11 and captures an image of a subject to be visually identified by the patient.

The internal body device 20 includes the receiver 23 made up of a secondary coil for receiving an electromagnetic wave from the external body device 10; a control unit 25 that extracts, from the electromagnetic wave received by the receiver 23, an electrical stimulation pulse and a multiplexer control signal (hereinafter called a "control signal") for distributing an electrical stimulation pulse to respective designated electrodes, designated electrodes and that extracts electric power; a substrate 21 on which there are formed a plurality of electrodes 27 for outputting an electrical stimulation pulse; a multiplexer 40 that is a controller for distributing the electrical stimulation pulse to respective electrodes 27; a mount 60 that is interposed between the substrate 21 and the multiplexer 40 for electrically connecting the substrate 21 to the multiplexer 40; a cable 22; an opposing electrode 26; and others.

The substrate 21 has a base portion that is formed by processing a highly biocompatible resin (e.g., polyimide, etc.) so as to be foldable into a predetermined thickness and in the shape of an elongated plate, and a plurality of lead wires 21a and the electrodes 27 are formed on the base portion. In relation to the lead wires 21a shown in FIGS. 2A and 2B, a corrosion resistant metallic material is deposited on the base portion by use of a well-known photoresist technique, a well-known vacuum evaporation technique, a well-known sputtering technique, and the like. After a conductive layer has been formed on the metallic material, a mask is removed, and an insulating layer is applied to or affixed to the conductive layer to a thickness by means of which the conductive layer is cladded. Further, a highly biocompatible insulating material; for instance, polyimide, parylene, etc., is used for the insulating layer.

A through holes is made in an insulating layer located at an end of the conductive layer by a method, such as RIE (Reactive Ion Etching), etc., thereby leaving an end of the conductive layer exposed. A conductive material is stacked (deposited) on the thus-exposed end, thereby creating an electrical junction between the mount 60 and the substrate 21. When there is a desire to lay out the plurality of lead wires 21*a* in a three-dimensional manner (in other words, a desire to perform three-dimensional wiring), the above processing is repeatedly performed a plurality of times.

As shown in FIG. 2A, the plurality of electrodes 27 are arranged in a matrix pattern along a longitudinal direction of the substrate 21 or arranged so as to be two-dimensionally staggered at regular intervals, whereby an electrode array is created. The number of electrodes 27 to be fabricated ranges from tens of electrodes to hundreds of electrodes according to a resolution of vision regeneration. The electrodes 27 can also be made in a greater number according to a footprint of the electrodes and a wiring technique. The electrodes 27 are formed at ends of the respective lead wires 21*a* from a conductive material exhibiting a superior biocompatibility and superior corrosion resistance, like gold and platinum.

The flat-plate-like mount 60 is formed from a material, such as ceramics, that exhibits an insulating characteristic and hermeticity against gas and moisture (i.e., low permeability) and that exhibits bio compatibility. Wires 61 to be electrically connected to terminals of a pattern wire of the multiplexer 40 are formed so as to penetrate through the mount 60 in its thicknesswise direction (a wall thickness). The substrate 21 and the multiplexer 40 are electrically connected together by way of the wires 61. The wires 61 are formed by charging a conductive material into through holes provided at locations corresponding to the respective terminals of the pattern wires of the multiplexer 40.

The wires 61 are formed in (filled into) the respective through holes of the mount 60 while the mount 60 is attached onto the substrate 21 and while the multiplexer 40 is attached onto the mount 60. The wires 61 are formed by connection of two types of conductive materials. Specifically, the wires 61 include wires 61*a* (first wires) filled from openings (apertures of the through holes) on a side of the substrate facing the multiplexer 40 to a predetermined depth and wires 61*b* (second wires) filled into the through holes from a remaining side of the substrate 21 where no wires 61*a* are formed. The wires 61*a* are made constituent with the mount 60 in terms of a coefficient of thermal expansion and are formed by sintering a first conductive material that is not fused at a sintering temperature of the mount. In the meantime, the wires 61*b* are formed by sintering a second conductive material exhibiting biocompatibility (see FIG. 3).

For instance, a material used as the first conductive material includes one type or a plurality of types of silver, tungsten, or molybdenum mixed as a primary material and that is also mixed with a predetermined quantity of additive (a secondary material) for assuring consistency with the mount 60 in terms of a coefficient of thermal expansion. Copper, metal oxide, etc., is preferably used as the secondary material. Further, a material differing from the first conductive material is used as the second conductive material. A metallic material exhibiting a superior biocompatibility; for instance, gold, platinum, etc., is used as the second conductive material. Such first and second conductive materials are prepared as paste that is produced by dispersing a metallic material as a metallic powder into an organic carrying liquid (a mixture), and by adding a viscosity control diluents to a resultant mixture. The organic carrying liquid is produced by dissolving an organic binder, such as a cellulose-based or acrylic material, into an organic solvent, such as terpineol, trimethylbenzene, and methyl ethyl ketone.

The multiplexer 40 built from a semiconductor integrated circuit distributes an electrical stimulation pulse (a stimulation electric current) for stimulating the cells forming the retina to the respective electrodes 27 according to an electrical stimulation pulse and a control signal sent from the control unit 25. The multiplexer 40 is connected to the control unit 25 (receiver 23) by way of the cable 22, and is electrically connected to the lead wires 21*a* and the respective electrodes 27 by way of the wires 61 of the mount 60. The cable 22 is covered with an insulating material exhibiting a high biocompatibility.

Figure 4A:
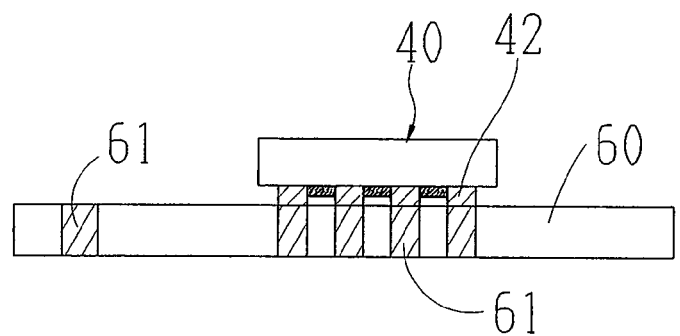
FIGS. 4A, 4B, and 4C are explanatory views of procedures for manufacturing the internal body device.
Figure 4B:
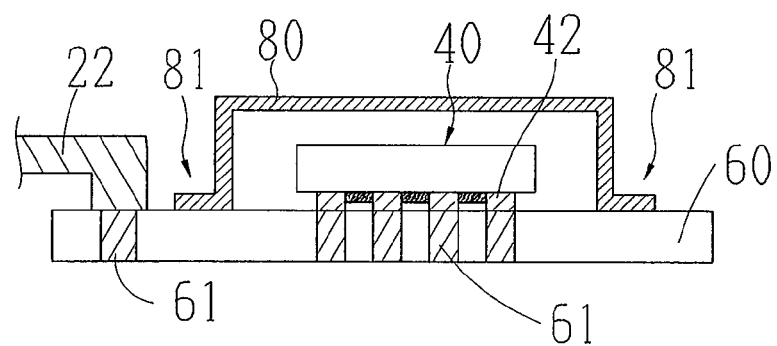
Figure 4C:
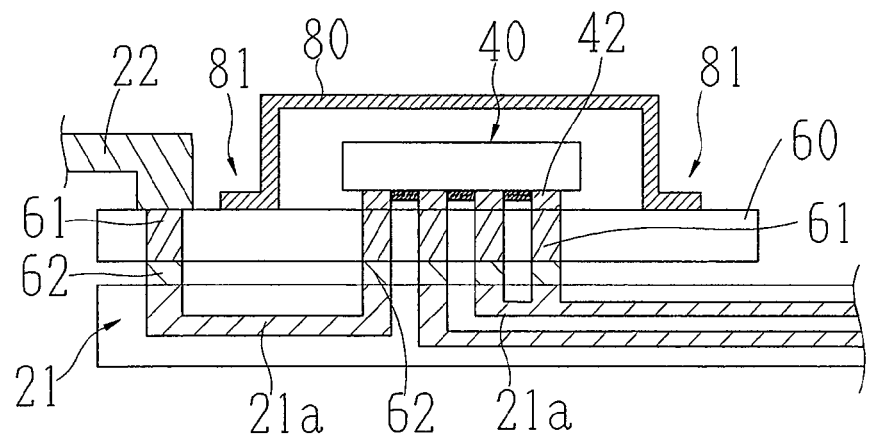

A cover member 80 is formed from a material (metal) exhibiting a high biocompatibility and high hermeticity; for instance, ceramics, titanium, platinum, gold, and the like, and molded into a shape covering the multiplexer 40. As shown in FIGS. 4A, 4B, and 4C, the cover member 80 is formed so as to assume a hat-shaped cross sectional profile and have a flange 81 used for being bonded to the mount 60, whereby an internal space capable of accommodating the multiplexer 40 is made. It is desirable that a height of the internal space will be slightly higher than an upper surface of the multiplexer 40 bonded to the mount 60. Such a cover member 80 is formed by a known ceramic processing technique, a known thin plate working technique, etc. The cover member 80 is thinly formed so as to assume preferably a thickness (wall thickness) from tens of micrometers to 500 micrometers and more preferably from about 100 micrometers to 200 micrometers.

The multiplexer 40 is hermetically sealed by the cover member 80 and the mount 60.

The control unit 25 includes a circuit for dividing electrical stimulation pulse data and electric power from an electromagnetic wave received by the receiver 23, a conversion circuit for acquiring an electrical stimulation pulse used for generating sense of vision from the electrical stimulation pulse data and a control signal, and a semiconductor integrated circuit (LSI) having an electric circuit, etc., for sending an electrical stimulation pulse and a control signal to the multiplexer 40. The multiplexer 40 receiving the electrical stimulation pulse and the control signal generated by the control unit 25 sends (distributes) the electrical stimulation pulse to the respective electrodes 27 according a control signal. The respective electrodes 27 are independently connected to the multiplexer 40 by way of the wires 61 of the mount 60.

A method for manufacturing the vision regeneration assist apparatus 1 having the foregoing configuration is now described with an emphasis on procedures for manufacturing the mount 60. FIGS. 3A, 3B, 3C, and 3D are descriptive views of procedures for manufacturing the mount 60. The mount 60 is formed from fine ceramics (new ceramics) by a known molding technique. In the embodiment, there is provided an explanation about; as an example, a case where oxide ceramics (aluminum) are used as a material. In addition to the oxide ceramics, a material exhibiting an insulation characteristic and biocompatibility, such as glass ceramic, is preferred to be selected.

First, a plate-shaped layer is formed by use of aluminum powder. The mount 60 is formed by piling a plurality of plate-shaped layers into an integrated piece. In the embodiment, three layers are piled, to thus form the mount 60. A layer positioned closest to the multiplexer 40 is taken as a first layer 62; an intermediate layer is taken as a second layer 63; and a layer positioned closest to the substrate 21 is taken as a third layer 64. The respective layers 62 to 64 are formed by a well-known processing technique, such as pressing or rolling aluminum powder. The respective layers 62 to 64 are processed so as to assume a uniform thickness; for instance, 0.15 mm. In addition to the structure mentioned above, the mount 60 may be formed from at least one layer. In this case, thickness of each of the layers is set in such a way that the mount 60 produced after molding assumes a desired thickness. When the mount 60 is formed from a plurality of layers, the layers may assume a uniform thickness or different thicknesses.

A plurality of through holes 70 are formed at a position on the respective layers 62 to 64 that corresponds to the location of a terminal of the pattern wiring of the multiplexer 40 (through holes 70a to 70c are formed in the respective layers 62 to 64 in their thickness direction). The through holes 70 can be formed by means of punching, microdrilling, laser irradiation, etc. For instance, the through holes 70 having a diameter of about 100 to 200 micrometers are formed in numbers at the same location on each of the layers 62 to 64.

The through holes 70a of the layer 62 and the through holes 70b of the layer 63 are now filled with the first conductive material. A material that is a mixture of silver, tungsten, or molybdenum, and a predetermined additive for controlling a coefficient of thermal expansion, like copper, is used as a first conductive material. Controlling a coefficient of thermal expansion (achieving consistency) means that a coefficient of thermal expansion of the first conductive material is controlled so as to prevent occurrence of distortion or cracks, which would otherwise be caused by thermal expansion of the mount 60 and thermal expansion of the first conductive material and which would pose an impediment to mounting the multiplexer 40 on the mount 60, when the mount 60 is sintered at high temperatures with the first conductive material filled in the through holes of the mount.

When a large difference exists between the material forming the mount 60 and the first conductive material in terms of a coefficient of thermal expansion, the mount 60 and the wires 61a formed from the first conductive material thermally expand when sintered, to thus interfere with each other. The interference in turn causes distortion or cracking. For this reason, according to the exemplary embodiment, the coefficient of thermal expansion of the wires 61a is adjusted in such a way that the material forming the mount 60 and the first conductive material become substantially equal to each other in terms of a coefficient of thermal expansion, thereby preventing occurrence of distortion or cracking.

Figure 3A:
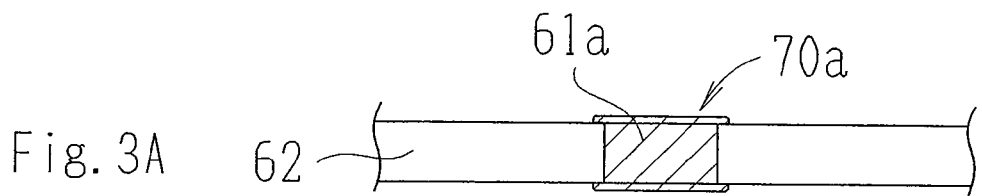
FIGS. 3A, 3B, 3C, and 3D are explanatory views of procedures for manufacturing a mount.

Metal powder forming the foregoing first conductive material is dispersed in the organic carrying liquid in which a resin to serve as an organic binder is dissolved in an organic solvent, thereby preparing paste. The shape of the first conductive material can thereby be freely deformed. Next, as shown in FIG. 3A, paste of the first conductive material is filled into the through holes 70a so as to prevent occurrence of clearance. Paste of the first conductive material for making the wires 61a is filled into the through holes 70b of the second layer 63 without involvement of clearance. At this time, it is preferable to charge a larger amount of paste of the first conductive material into a boundary between the overlapping layers 62 and 63 in consideration of alignment therebetween. The adjacent wires 61a are thus preferably connected to each other as a result of the layers 62 and 63 overlapping each other. Moreover, it is also preferable to charge a larger amount of paste into a boundary between the layers 63 and 64, in consideration of alignment therebetween.

In the present embodiment, the paste of the first conductive material is first filled into two layers of the three layers forming the mount 60. Subsequently, the paste of the second conductive material is filled into a remaining one layer. However, charging of paste is not limited to the sequence mentioned above. For instance, it may also be possible to charge the paste of the first conductive material into, among the three layers forming the mount 60, one layer adjoining the multiplexer 40 and subsequently charge the paste of the second conductive material into the remaining two layers. Alternatively, it may also be possible to charge the paste of the first conductive material into an arbitrary position in, among the three layers, one layer adjoining the multiplexer 40 and subsequently charge the paste of the second conductive material into the remaining layers.

In addition, a depth to which the second conductive material is to be filled into the through holes 70 from the substrate 21 is determined so as to prevent occurrence of, at least, interference between a body fluid and the first conductive material, which would otherwise arise when the body fluid invades the boundary between the substrate 21 and the mount 60. The reliability of the internal body device 20 is thus enhanced by determining the depth in such a way.

Figure 3B:
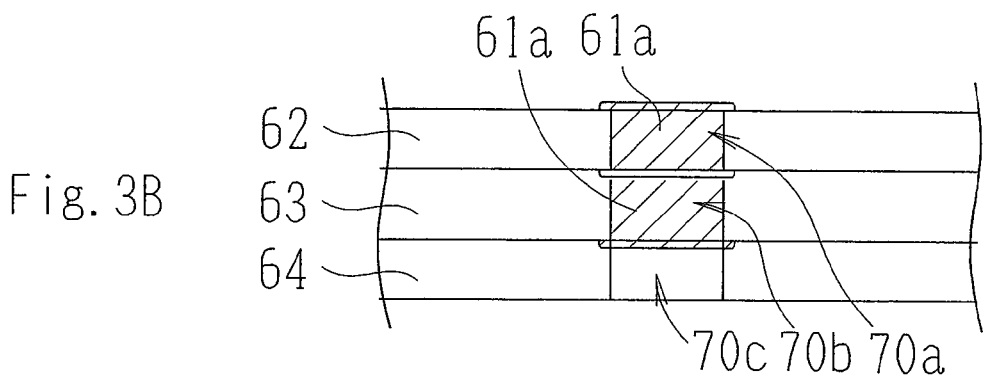

As mentioned above, the layers 62 to 64 are superimposed one on top of the other in such way that positions of the respective through holes 70a to 70c coincide with each other as shown in FIG. 3B while the through holes 70a and 70b are filled with the first conductive material. The layers are then subjected to thermal compression bonding at a predetermined temperature and under predetermined pressure for several minutes, to thus be integrated into a single piece. Though unillustrated, a preferable way is to print a connection between the layer 62 and the layer 63 with a metallic film formed from silver, tungsten, molybdenum, etc., in a yet-to-be-sintered state where through holes 70a and 70b are filled with the paste of the first conductive material. A state of electrical connection between the layer 62 and the layer 63 is thereby improved. The metallic films formed at the locations of the adjoining through holes 70a and 70b are formed within a range where the metallic films do not contact each other.

The thus-superimposed layers 62 to 64 are subjected to first sintering by high-temperature heating in a known furnace. When alumina is used for the layers 62 to 64, a temperature of the furnace is set to; for instance, 1500 to 1800° C., (1500 to 1600° C. for the case of alumina that is 90 to 97% pure and 1500 to 1800° C. for the case of high purity alumina that is 99% or more pure). By high-temperature heating of the furnace, alumina slightly expands, and the solvent of the paste of the first conductive material evaporates, to thus be sintered. An inner diameter of each of the through holes 70 becomes smaller by contraction due to cooling after heating, whereby the wires 61a are formed in the through holes 70a and 70b without clearance (a state of one of the through holes 70 achieved before contraction is denoted by a dotted line in FIG. 3C, and a state of the same achieved after contraction is designated by a solid line in the same drawing).

The wires 61a are formed, on the side of the layer where the multiplexer 40 is to be placed, from the first conductive material made consistent with alumina in terms of a coefficient of thermal expansion. As a result, occurrence of distortion or cracking in the surface of the mount 60 is prevented, whereby the surface of the layer 62 becomes flat. The multiplexer 40 and the mount 60 can preferably, electrically be connected together. Further, the surface of the layer 64 where the unfilled through hole 70c is formed also becomes flat. Hence, the substrate 21 and the mount 60 are preferably connected together.

Figure 3C:
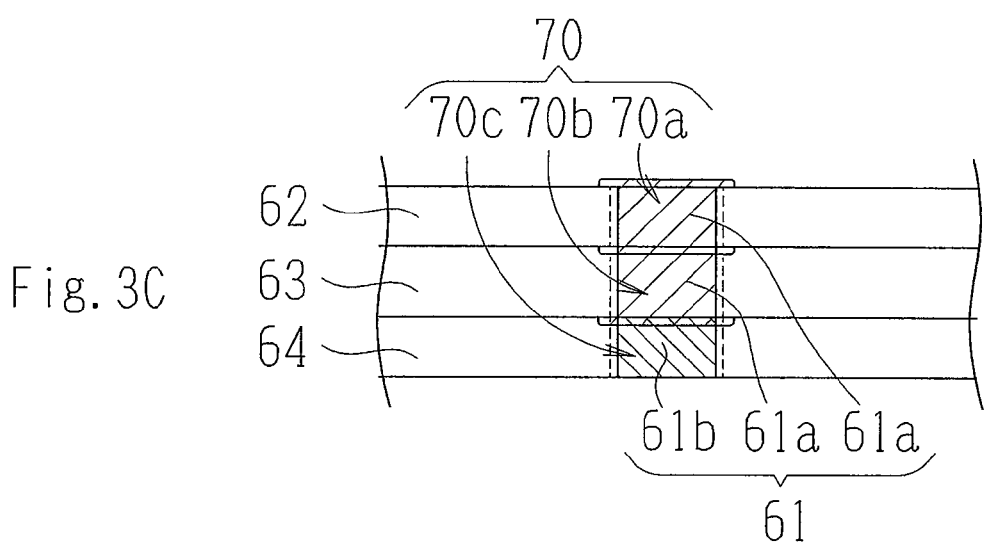

As shown in FIG. 3C, the through holes 70c are filled with paste including platinum that is the second conductive material while the layers 62 to 64 and the wires 61a are sintered through first sintering operation. The paste is also produced by dispersing metallic powder (platinum) into an organic carrying liquid in which a resin to serve as an organic binder is dissolved in an organic solvent. The paste can be freely deformed into any shape.

The layers are subjected to second sintering while the through holes 70c are filled with platinum. The temperature of the furnace is set, at this time, so as to become higher than a temperature at which sintering of platinum is started and lower than a fusing point of platinum. The solvent of the platinum paste evaporates during second sintering operation, whereby platinum is sintered. The wires 61b are thereby formed in the through holes 70c. Only platinum is left after second sintering, whereby the wires 61b are formed from only platinum that exhibits bio compatibility.

Incidentally, a coefficient of thermal expansion of platinum is higher than a coefficient of thermal expansion of alumina. However, the mount 60 is sinter-hardened by first sintering operation, whereby the shape of the mount is fixed. Therefore, the shape of the mount 60 remains unchanged during second sintering. For this reason, the wires 61b formed as a result of sintering of platinum that is the second conductive material are placed in the through holes 70c without clearance, and the surface of the layer 64 to which the substrate 21 is to be connected is kept flat. The wires 61a formed from the first conductive material produced by first sintering and the wires 61b formed from platinum are bonded together by second sintering, whereby the wires 61a and 61b are electrically connected together.

Figure 3D:
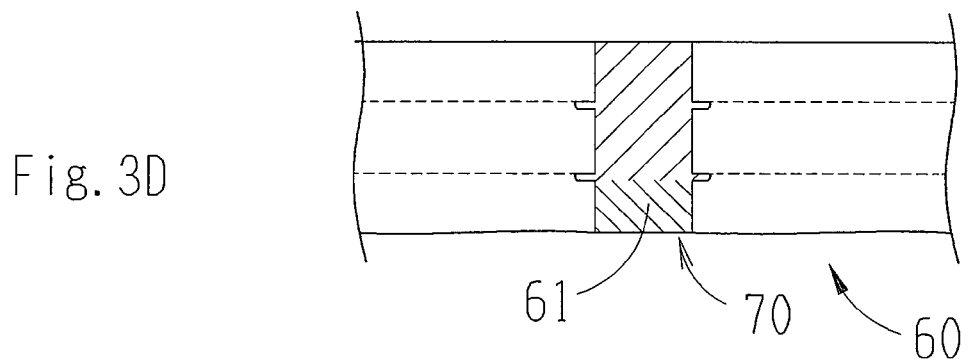

As mentioned above, after the wires 61 have been made on the mount 60 formed from the layers 62 to 64, any excess is finally removed by cutting, grinding, and the like, whereupon the mount 60, such as that shown in FIG. 3D, is completed.

The mount 60 fabricated as mentioned above and the multiplexer 40 are then bonded together. FIGS. 4A to 4C are explanatory views of procedures for manufacturing the internal body device 20. First, the mount 60 and the multiplexer 40 are bonded together as shown in FIG. 4A. Bumps 42 are previously formed from gold, etc., at terminals (bonding pads) of the pattern wires of the multiplexer 40 by use of an existing technique. The wires 61 of the mount 60 and the bumps 42 are aligned and brought into contact with each other while a bump-formed surface is oriented opposite the mount 60. Since the surface (an exterior surface of the layer 62) of the mount 60 is formed flat, respective terminals of the multiplexer 40 are preferably connected by way of the bumps 42.

Subsequently, the mount 60 and the multiplexer 40 are bonded together by flip-chip bonding. During flip-chip bonding, the terminals of the pattern wires and the wires 61, which are metals, are firmly bonded together at high temperatures and under high pressure by way of the bumps 42. Clearance between the multiplexer 40 and the mount 60 is filled with a filler (an adhesive) exhibiting an insulating characteristic. A degree of bonding between the multiplexer 40 and the mount 60 is increased by the filler, and the pattern wires on the multiplexer 40 are protected during bonding. Further, as a result of the clearance being filled with the filler, an air existing in the area to be bonded is eliminated. Bonding between the multiplexer 40 and the mount 60 may also involve use of ultrasonic waves, high pressure, and heat. Alternatively, there may also be adopted a configuration in which epoxy, etc., flows into the clearance between the multiplexer 40 and the mount 60 after bonding.

As shown in FIG. 4B, the mount 60 and the cover member 80 are now bonded together. Processing pertaining to the process is performed in an atmosphere of inactive gas (argon or a nitrogen gas). Argon is used as an inactive gas in the embodiment. An internal space of the cover member 80 is thereby filled with argon. An unillustrated metallic layer formed on the mount 60 in the argon atmosphere by metallization processing and the flange 81 of the cover member 80 are aligned to each other and brought into contact with each other. Subsequently, the flange 81 is traced while heated and pressurized by an unillustrated roller, whereupon the metallic layer formed by metallization processing and the flange 81 are seam-bonded.

The mount 60 and the cover member 80 are bonded as mentioned above, whereby the multiplexer 40 is sealed and protected against the outside. Specifically, the mount 60 and the cover member 80 form a case for hermetically sealing the multiplexer 40. Further, the wire 61 of the mount 60 and the cable 22 are bonded in advance. A leading end of the cable 22 is brought into contact with the wire 61 and bonded under high pressure and at high temperature. The cable 22 and the wire 61, which are metals, are firmly bonded together.

In the embodiment, the wire 61 of the mount 60 is formed as a bond between the first conductive material whose coefficient of thermal expansion is adjusted and the second conductive material exhibiting biocompatibility. It is likewise preferable to form, from the second conductive material exhibiting bio compatibility, a side of the wire 61 that is to be connected to the cable 22 and that has the potential for being subject to a contact with at least a body fluid.

Finally, as shown in FIG. 4C, the substrate 21 is bonded to a surface of the mount 60 that is opposite to the surface where the multiplexer 40 is mounted. Bumps 62 previously formed on the mount 60 and externally-exposed portions of the lead wires 21a are, at this time, aligned and brought into contact with each other in the same manner as in the previously-described process. Since the surface of the mount 60 (the surface of the layer 64) is formed flat by first sintering operation, the mount 60 and the substrate 21 are preferably, electrically connected together.

Subsequently, the contact is subjected to ultrasonic waves, etc., whereby the mount 60 and the substrate 21 are bonded together. Clearance between the mount 60 and the substrate 21 is at this time filled with an epoxy resin exhibiting biocompatibility. In relation to bonding of the mount 60 to the substrate 21, there is adopted a configuration in which the bumps 62 are formed on the mount 60. However, bonding of the mount to the substrate is not limited to the configuration. There may also be adopted a configuration in which bumps are formed on the exposed lead wires 21a of the substrate 21.

After a series of bonding operations mentioned above, the entire substrate 21 exclusive of the electrodes 27 is packaged with a highly biocompatible resin (silicone, parylene, polyimide exhibiting high biocompatibility, and the like). As a result of the substrate being packed with the resin, the multiplexer 40 is further hermetically sealed so as not to contact a living body.

Figure 5:
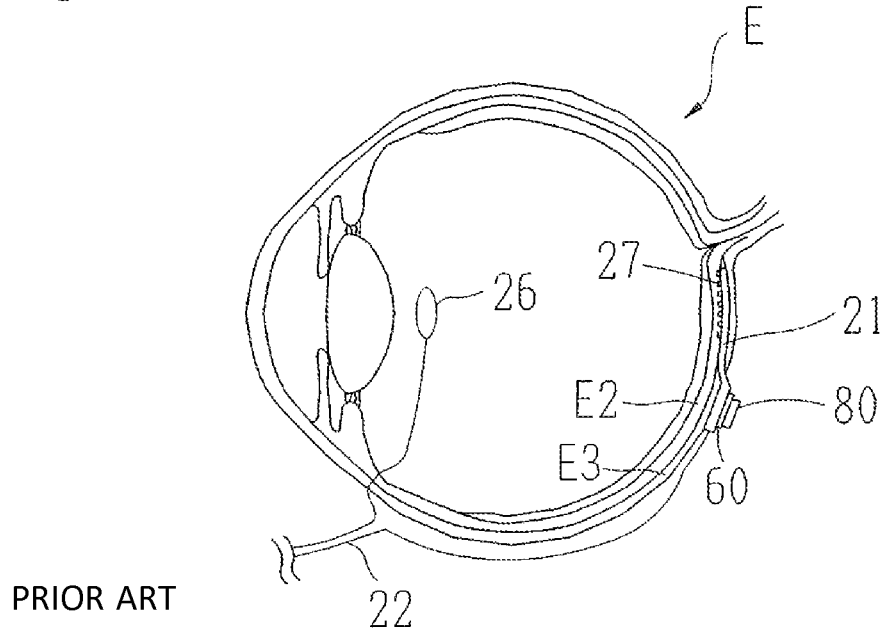
FIG. 5 is a diagrammatic illustration of the internal body device implanted in an eyeball.

FIG. 5 is a diagrammatic illustration of the internal body device 20 implanted in an eyeball E. A thin area of the substrate 21 where the electrodes 27 are placed is placed on a choroidea E2. In the meantime, a thick portion of the substrate 21 where the multiplexer 40, and others, are placed is placed outside a sclera E3. In this case, the body fluid may flow into the mount 60 by way of the substrate 21. However, the wires 61b formed from platinum exhibiting superior biocompatibility are placed on the side of the mount 60 facing the substrate 21. Accordingly, even when the body fluid has reached the wire 61b, the living body is not adversely affected. If there is a possibility that the body fluid will invade an interior of the through holes 70 even to a small extent, it is preferable to form the wire 61b, which is formed as a result of sintering of the second conductive material exhibiting superior biocompatibility, as deeply as possible into ends of the through holes 70 having the potential of contacting the body fluid.

Figure 6:
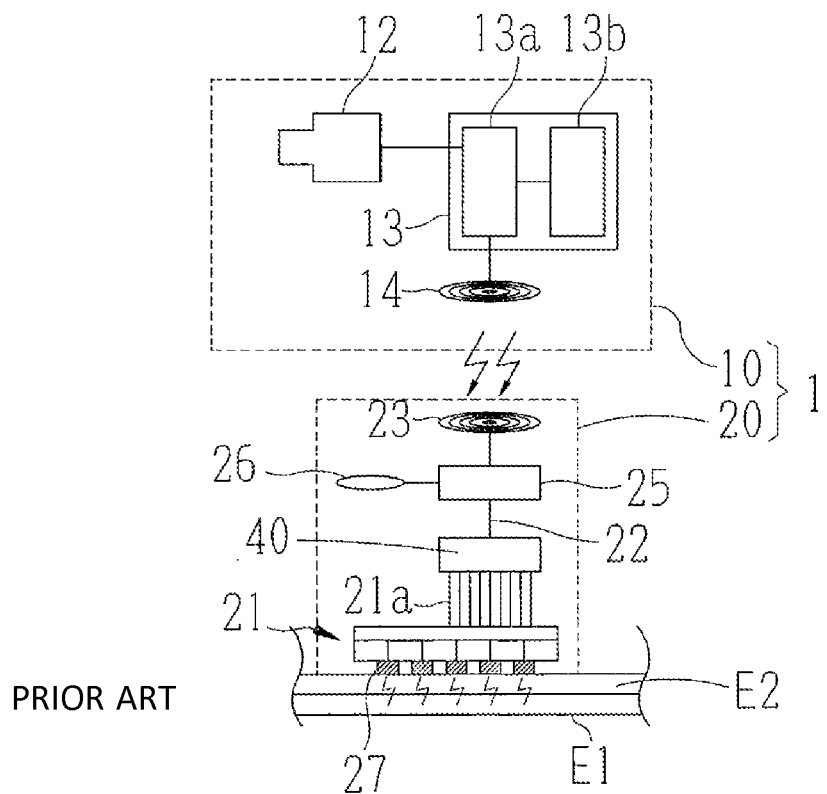
FIG. 6 is a block diagram of a control system.

Operation of the vision regeneration assist apparatus having a configuration, such as that mentioned above, for regenerating vision is now described. FIG. 6 is a block diagram of a control system. Photograph data (image data) pertaining to a subject photographed by the image-taking device 12 are sent to the pulse signal conversion unit 13*a*. The pulse signal conversion unit 13*a* converts the data into a signal in a predetermined range required by the patient to visually recognize the photographed subject (electrical stimulation pulse data) and transmits the signal as an electromagnetic wave from the transmitter 14 to the internal body device 20.

Concurrently, the pulse signal conversion unit 13*a* converts the electric power supplied from the battery 13*b* into a signal (electric power) having a range differing from the range of the signal (the electrical stimulation pulse data) and transmits the signal as an electromagnetic wave to the internal body device 20 along with the electrical stimulation pulse data.

In the internal body device 20, the receiver 23 receives the electrical stimulation pulse data and the electric power transmitted from the external body device 10 and transmits the thus-received data and electric power to the control unit 25. The control unit 25 extracts, from the received signal, a signal having the range used by the electrical stimulation pulse data. The control unit 25 generates, based on the extracted electrical stimulation pulse data, an electrical stimulation pulse to be distributed to the respective electrodes 27 and a control signal for controlling distribution of the electrical stimulation pulse and sends the thus-generated pulse and the control signal to the multiplexer 40. According to the control signal, the multiplexer 40 distributes the electrical stimulation pulse to the respective electrodes 27 and lets the respective electrodes 27 output the electrical stimulation pulse. The cells forming the retina are thereby stimulated, whereby the patient acquires vision.

Figure 7:
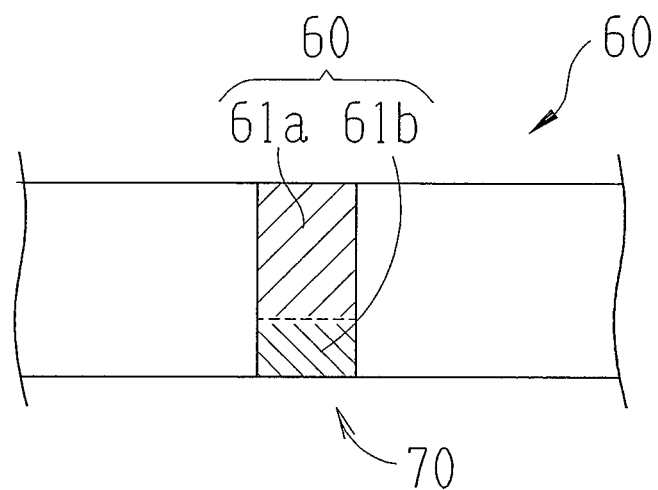
FIG. 7 is an enlarged cross sectional view of a neighborhood of a through holes of a second embodiment of the mount.

In the foregoing descriptions, an explanation is given to the case where the mount 60 is built into a three-layer structure. However, the mount 60 may also assume a single-layer structure. FIG. 7 is an enlarged cross sectional view of a neighborhood of one of the through holes 70 of the mount 60 according to the second embodiment. In this case, each of the through holes 70 is formed in the mount 60 having a single-layer structure and a predetermined thickness (e.g., a thickness of 0.45 mm). The mount is subjected to first sintering while the first conductive material is filled to an arbitrary position in each of the through holes 70 (facing the multiplexer 40). Next, the second conductive material is filled into a remaining of each of the through holes 70 (facing the substrate 21) that is not yet filled with the first conductive material, and the mount is subjected to second sintering. As a result, the mount 60 that yields an advantage similar to that mentioned above can be formed more simply.

Figure 8:
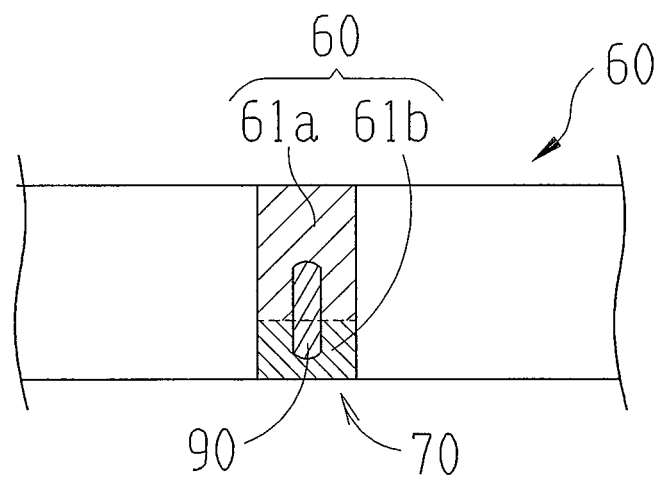
FIG. 8 is an enlarged cross sectional view of a neighborhood of a through holes of a third embodiment of the mount.

In addition, the first conductive material and the second conductive material may also be firmly connected together by way of a bulk, conductive connection member 90. FIG. 8 is an enlarged view of a neighborhood of one of the through holes 70 of the mount 60 according to a third embodiment. It is preferable to use metal exhibiting biocompatibility, like platinum, for the connection member 90. In this case, a portion of the connection material 90 is embedded while the paste-like first conductive material is filled to an arbitrary position in one of the through holes 70 of the mount 60 (facing the multiplexer 40). The mount is subjected to first sintering in this state. Subsequently, the second conductive material is filled to a remaining (facing the substrate 21) of one of the through holes 70 that is not yet filled with the first conductive material, and the mount is subjected to second sintering. As a result, the connection member 90 is packaged while extending over the first conductive material and the second conductive material. Therefore, the wires 61*a* and 61*b* that are formed from the first conductive material and the second conductive material after sintering assumes an improved state of physical connection, so that the wires become less likely to come off from the through holes 70. Further, a state of electrical connection is also improved further.

The present invention is applicable to any implantable apparatus for giving an electrical stimulation to a body tissue. For example, the present invention is applicable to an artificial middle ear for transmitting a sound wave to an auditory ossicle of a patient, a cardiac pacemaker implemented in a chest region of a patient for giving an electrical stipulation to a heart to suppress an occurrence of arrhythmic heartbeat, etc. are known. By installing the mount having the wiring structure described in the above exemplary embodiment to the implantable apparatus, superior electrical connection between an electric circuit and a substrate having electrodes by way of the mount can be maintained, and the implantable apparatus can be implanted with high reliability for a long period of time while preventing occurrence of invasion of a body fluid into the electronic circuit.

What is claimed is:

1. A vision regeneration assist apparatus for regenerating a patient's vision by giving an electrical stimulation to cells forming a retina, the apparatus comprising:
   a substrate including a plurality of electrodes;
   a control unit that controls an electrical stimulation pulse to be transmitted to the electrodes;
   a mount that is formed from a ceramic sintered element made of an insulating material forming a hermetic bottom for isolating and sealing the control unit from outside, the mount including:
   a plurality of through holes formed through the mount in a thickness direction,
   an upper surface on which the control unit is placed; and
   a lower surface on which the substrate is placed;
   an internal conductor that is filled into the through holes of the mount to electrically connect the control unit with wires extending from the electrodes and that includes:
   a first conductive material which is filled to a predetermined depth from openings of the through holes at the upper surface of the mount, the first conductive material including a primary member which takes at least one type of conductive material, which is not fused at a sintering temperature of the mount, the first conductive material including at least one type of molybdenum, tungsten, and silver, the first conductive material filled to the predetermined depth having a uniform coefficient of thermal expansion approximately equal to a coefficient of thermal expansion of a material forming the mount; and
   a second conductive material which is formed from a conductive material that is filled into a remaining of the through holes, which faces the substrate and the remaining of the through holes being other than a part in which the first conductive material is filled to the predetermined depth, the second conductive material exhibiting biocompatibility, the second conductive material including one of platinum and gold; and
   wherein the first conductive material is different from the second conductive material.

2. The apparatus according to claim 1, wherein
   the first conductive material includes a secondary member for performing adjustment in such a way that a coefficient of thermal expansion of the first conductive material approximately becomes equal to a coefficient of thermal expansion of a material forming the mount, and the second conductive material does not include the secondary member.

3. The apparatus according to claim 2, wherein a depth to which the second conductive material is filled into the substrate is larger than a depth to which the first conductive material is filled into the substrate.

4. The apparatus according to claim 1, wherein a depth to which the second conductive material is filled into the substrate is larger than a depth to which the first conductive material is filled into the substrate.

5. The apparatus according to claim 4, wherein the internal conductor includes a conductive connection block that is surrounded by the first and second conductive material while extending over the first conductive material and the second conductive material to connect the first conductive material to the second conductive material.

6. The apparatus according to claim 1, wherein:
the mount includes at least three layers, each of which is formed from the ceramic sintered element, the plurality of through holes are formed through the at least three layers;
the first conductive material is filled into the plurality of through holes of two of the at least three layers; and
the second conductive material is filled into the plurality of through holes of one of the at least three layers other than the two of the at least three layers.

7. An implantable apparatus for giving an electrical stimulation to a body tissue, comprising:
a substrate including a plurality of electrodes;
a control unit that controls an electrical stimulation pulse to be transmitted to the electrodes;
a mount that is formed from a ceramic sintered element made of an insulating material forming a hermetic bottom for isolating and sealing the control unit from outside, the mount including:
a plurality of through holes formed through the mount in a thickness direction,
an upper surface on which the control unit is placed; and
a lower surface on which the substrate is placed;
an internal conductor that is filled into the through holes of the mount to electrically connect the control unit with wires extending from the electrodes and that includes:
a first conductive material which is filled to a predetermined depth from openings of the through holes at the upper surface of the mount, the first conductive material including a primary member which takes at least one type of conductive material, which is not fused at a sintering temperature of the mount, the first conductive material including at least one of molybdenum, tungsten and silver, the first conductive material filled to the predetermined depth having a uniform coefficient of thermal expansion approximately equal to a coefficient of thermal expansion of a material forming the mount; and
a second conductive material which is formed from a conductive material that is filled into a remaining of the through holes, which faces the substrate and the remaining of the through holes being other than a part in which the first conductive material is filled to the predetermined depth, the second conductive material exhibiting biocompatibility, the second conductive material including one of platinum and gold; and
wherein the first conductive material is different from the second conductive material.

8. The apparatus according to claim 7, wherein
the first conductive material includes a secondary member for performing adjustment in such a way that a coefficient of thermal expansion of the first conductive material approximately becomes equal to a coefficient of thermal expansion of a material forming the mount, and
the second conductive material does not include the secondary member.

9. The apparatus according to claim 8, wherein a depth to which the second conductive material is filled into the substrate is larger than a depth to which the first conductive material is filled into the substrate.

10. The apparatus according to claim 7, wherein:
the mount includes at least three layers, each of which is formed from the ceramic sintered element, the plurality of through holes are formed through the at least three layers;
the first conductive material is filled into the plurality of through holes of two of the at least three layers; and
the second conductive material is filled into the plurality of through holes of one of the at least three layers other than the two of the at least three layers.

* * * * *